(12) United States Patent
Flohr et al.

(10) Patent No.: US 6,624,163 B2
(45) Date of Patent: Sep. 23, 2003

(54) BENZOTHIAZOLE DERIVATIVES

(75) Inventors: Alexander Flohr, Basel (CH); Roland Jakob-Roetne, Inzlingen (DE); Roger David Norcross, Rheinfelden (CH); Claus Riemer, Freiburg (DE)

(73) Assignee: Hoffman-La Roche Inc., Nutley, NJ (US)

( * ) Notice: Subject to any disclaimer, the term of this patent is extended or adjusted under 35 U.S.C. 154(b) by 0 days.

(21) Appl. No.: 10/295,500

(22) Filed: Nov. 15, 2002

(65) Prior Publication Data

US 2003/0134855 A1 Jul. 17, 2003

(30) Foreign Application Priority Data

Nov. 29, 2001 (EP) .............................. 01128338

(51) Int. Cl.⁷ ..................... A61K 31/5377; A61P 25/28; C07D 413/02; C07D 413/14
(52) U.S. Cl. ..................... 514/233.8; 544/135
(58) Field of Search ................. 548/135; 514/233.8

(56) References Cited

FOREIGN PATENT DOCUMENTS

| EP | 113219 | 7/1984 |
|---|---|---|
| EP | 0 295 656 | 12/1988 |
| EP | 0 343 893 | 11/1989 |
| WO | WO 01 97786 | 12/2001 |

OTHER PUBLICATIONS

Alanine et al, *Chemical Abstracts*, vol 136, No. 69803, 2001.*
Poulsen et al., Bioorganic & Medicinal Chemistry, 6, pp. 619–641 (1998).
Müller et al., Bioorganic & Medicinal Chemistry, 6, pp. 707–719 (1998).
Kim et la., J. Med. Chem., 41, pp. 2835–2845 (1998).
Li et al., J. Med. Chem., 41, pp. 3186–3201 (1998).
Baraldi et al., J. Med. Chem., 41, pp. 2126–2133 (1998).
Li et al., J. Med. Chem., 42, pp. 706–721 (1999).
Baraldi et al., J. Med. Chem., 39, pp. 1164–117 (1996).
Colotta et al., Arch. Pharm. Pharm. Med. Chem., 332, pp. 39–41 (1999).
Auchampach et al., Am. J. Physiol., 276, pp. H1113–H1116 (1999).
Haas et al., Naunyn Schmiedeberg's Arch. Pharmacol., 362, pp. 375–381 (2000).
Dionisotti et al., Br. J. Pharmacol., 121, pp. 353–360 (1997).
Pier Giovanni Baraldi, et al., Drug Development Research, vol. 46, No. 2, pp. 126–133 (1999).

* cited by examiner

*Primary Examiner*—Robert W. Ramsuer
(74) *Attorney, Agent, or Firm*—George W. Johnston; Patricia S. Rocha-Tramaloni; Lyman H. Smith

(57) ABSTRACT

The present invention relates to compounds of the formula

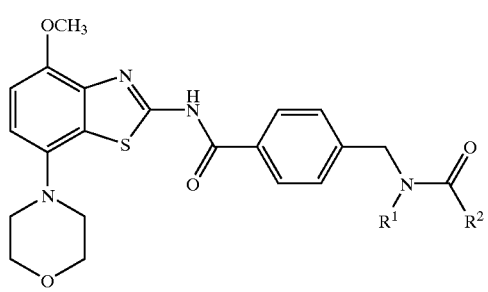

I wherein $R^1$ and $R^2$ are as defined herewithin. The compounds of formula I have been found to be adenosine receptor ligands. Specifically, the compounds of the present invention have a good affinity to the $A_{2A}$-receptor and they are therefore useful in the treatment of diseases, related to this receptor.

16 Claims, No Drawings

BENZOTHIAZOLE DERIVATIVES

BACKGROUND OF THE INVENTION

The present invention generally relates to benzothiazole compounds that are useful as adenosine receptor ligands. Specifically, the compounds of the present invention have a good affinity to the $A_{2A}$-receptor and a high selectivity to the $A_1$- and $A_3$ receptors.

Adenosine modulates a wide range of physiological functions by interacting with specific cell surface receptors. The potential of adenosine receptors as drug targets was first reviewed in 1982. Adenosine is related both structurally and metabolically to the bioactive nucleotides adenosine triphosphate (ATP), adenosine diphosphate (ADP), adenosine monophosphate (AMP) and cyclic adenosine monophosphate (cAMP); to the biochemical methylating agent S-adenosyl-L-methione (SAM); and structurally to the coenzymes NAD, FAD and coenzym A; and to RNA. Together adenosine and these related compounds are important in the regulation of many aspects of cellular metabolism and in the modulation of different central nervous system activities.

The receptores for adenosine have been classified as $A_1$, $A_{2A}$, $A_{2B}$ and $A_3$ receptors, belonging to the family of G protein-coupled receptors. Activation of adenosine receptors by adenosine initiates signal transduction mechanism. These mechanisms are dependent on the receptor associated G protein. Each of the adenosine receptor subtyps has been classically characterised by the adenylate cyclase effector system, which utilises cAMP as a second messenger. The $A_1$ and $A_3$ receptors, coupled with $G_i$ proteins inhibit adenylate cyclase, leading to a decrease in cellular cAMP levels, while $A_{2A}$ and $A_{2B}$ receptors couple to $G_s$ proteins and activate adenylate cyclase, leading to an increase in cellular cAMP levels. It is known that the $A_1$ receptor system include the activation of phospholipase C and modulation of both potassium and calcium ion channels. The $A_3$ subtype, in addition to its association with adenylate cyclase, also stimulates phospholipase C and so activates calcium ion channels.

The $A_1$ receptor (326–328 amino acids) was cloned from various species (canine, human, rat, dog, chick, bovine, guinea-pig) with 90–95% sequence identify among the mammalian species. The $A_{2A}$ receptor (409–412 amino acids) was cloned from canine, rat, human, guinea pig and mouse. The $A_{2B}$ receptor (332 amino acids) was cloned from human and mouse with 45% homology of human $A_{2B}$ with human $A_1$ and $A_{2A}$ receptors. The $A_3$ receptor (317–320 amino acids) was cloned from human, rat, dog, rabbit and sheep.

The $A_1$ and $A_{2A}$ receptor subtypes are proposed to play complementary roles in adenosine's regulation of the energy supply. Adenosine, which is a metabolic product of ATP, diffuses from the cell and acts locally to activate adenosine receptors to decrease the oxygen demand ($A_1$) or increase the oxygen supply ($A_{2A}$) and so reinstate the balance of energy supply: demand within the tissue. The actions of both subtyps is to increase the amount of available oxygen to tissue and to protect cells against damage caused by a short term imbalance of oxygen. One of the important functions of endogenous adenosine is preventing damage during traumas such as hypoxia, ischaemia, hypotension and seizure activity.

Furthermore, it is known that the binding of the adenosine receptor agonist to mast cells expressing the rat $A_3$ receptor resulted in increased inositol triphosphate and intracellular calcium concentrations, which potentiated antigen induced secretion of inflammatory mediators. Therefore, the $A_3$ receptor plays a role in mediating asthmatic attacks and other allergic responses.

Adenosine is a neuromodulator, able to modulate many aspects of physiological brain function. Endogenous adenosine, a central link between energy metabolism and neuronal activity, varies according to behavioral state and (patho)physiological conditions. Under conditions of increased demand and decreased availability of energy (such as hypoxia, hypoglycemia, and/or excessive neuronal activity), adenosine provides a powerful protective fedback mechanism. Interacting with adenosine receptors represents a promising target for therapeutic intervention in a number of neurological and psychiatric diseases such as epilepsy, sleep, movement disorders (Parkinson or Huntington's disease), Alzheimer's disease, depression, schizophrenia, or addiction An increase in neurotransmitter release follows traumas such as hypoxia, ischaemia and seizures. These neurotransmitters are ultimately responsible for neural degeneration and neural death, which causes brain damage or death of the individual. The adenosine $A_1$ agonists which mimic the central inhibitory effects of adenosine may therefore be useful as neuroprotective agents. Adenosine has been proposed as an endogenous anticonvulsant agent, inhibiting glutamate release from excitory neurons and inhibiting neuronal firing. Adenosine agonists therefore may be used as antiepileptic agents. Adenosine antagonists stimulate the activity of the CNS and have proven to be effective as cognition enhancers. Selective $A_{2a}$ antagonists have therapeutic potential in the treatment of various forms of dementia, for example in Alzheimer's disease, and of neurodegenerative disorders, e.g. stroke. Adenosine $A_{2a}$ receptor antagonists modulate the activity of striatal GABAergic neurons and regulate smooth and well-coordinated movements, thus offering a potential therapy for Parkinsonian symptoms. Adenosine is also implicated in a number of physiological processes involved in sedation, hypnosis, schizophrenia, anxiety, pain, respiration, depression, and drug addiction (amphetamine, cocaine, opioids, ethanol, nicotine, cannabinoids). Drugs acting at adenosine receptors therefore have therapeutic potential as sedatives, muscle relaxants, antipsychotics, anxiolytics, analgesics, respiratory stimulants, antidepressants, and to treat drug abuse. They may also be used in the treatment of ADHD (attention deficit hyper-activity disorder).

An important role for adenosine in the cardiovascular system is as a cardioprotective agent. Levels of endogenous adenosine increase in response to ischaemia and hypoxia, and protect cardiac tissue during and after trauma (preconditioning). By acting at the $A_1$ receptor, adenosine $A_1$ agonists may protect against the injury caused by myocardial ischemia and reperfusion. The modulating influence of $A_{2a}$ receptors on adrenergic function may have implications for a variety of disorders such as coronary artery disease and heart failure. $A_{2a}$ antagonists may be of therapeutic benefit in situations in which an enhanced antiadrenergic response is desirable, such as during acute myocardial ischemia. Selective antagonists at $A_{2a}$ receptors may also enhance the effectiveness of adenosine in terminating supraventricula arrhytmias.

Adenosine modulates many aspects of renal function, including renin release, glomerular filtration rate and renal blood flow. Compounds which antagonise the renal affects of adenosine have potential as renal protective agents. Furthermore, adenosine $A_3$ and/or $A_{2B}$ antagonists may be useful in the treatment of asthma and other allergic responses or and in the treament of diabetes mellitus and obesity.

Numerous documents describe the current knowledge on adenosine receptors, for example the following publications:

Bioorganic & Medicinal Chemistry, 6, (1998), 619–641,
Bioorganic & Medicinal Chemistry, 6, (1998), 7)7–719,
J. Med. Chem., (1998), 41, 2835–28470,
J. Med. Chem., (1998), 41, 3186–3201,
J. Med. Chem., (1998), 41, 2126–2133,
J. Med. Chem., (1999), 42, 706–721,
J. Med. Chem., (1996), 39, 1164–1171,
Arch. Pharm. Med. Chem., 332, 339–41, (1999),
Am. J. Physiol., 276, H1113–1116, (1999) or
Naunyn Schmied, Arch. Pharmacol. 362, 375–381, (2000).

SUMMARY OF THE INVENTION

The present invention relates to compounds of the formula

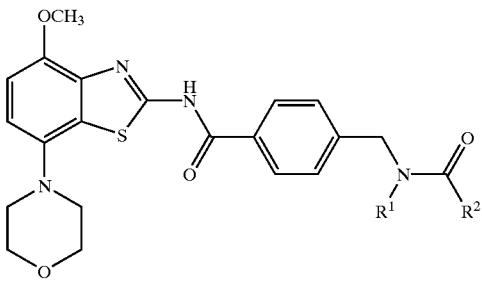

I wherein $R^1$ and $R^2$ are as defined herewithin.

The present invention relates to the compounds of formula I per se, the use of compounds of formula I and their pharmaceutically acceptable salts for the manufacture of medicaments for the treatment of diseases related to the adenosine $A_2$ receptor. The present invention further relates to the manufacture of compounds of formula I, medicaments based on compounds of formula I and their production, as well as the use of compounds of formula I in the control or prevention of illnesses based on the modulation of the adenosine system. Such illnesses include Alzheimer's disease, Parkinson's disease, Huntington's disease, neuroprotection, schizophrenia, anxiety, pain, respiration deficits, depression, drug addiction, such as amphetamine, cocaine, opioids, ethanol, nicotine, cannabinoids, or against asthma, allergic responses, hypoxia, ischaemia, seizure and substance abuse. Furthermore, compounds of the present invention maybe useful as sedatives, muscle relaxants, antipsychotics, antiepileptics, anticonvulsants and cardiaprotective agents for disorders such as coronary artery disease and heart failure. The most preferred indications in accordance with the present invention are those, which base on the $A_{2A}$ receptor antagonistic activity and which include disorders of the central nervous system, for example the treatment or prevention of Alzheimer's disease, certain depressive disorders, drug addiction, neuroprotection and Parkinson's disease as well as ADHD.

DETAILED DESCRIPTION OF THE INVENTION

The present invention relates to compounds of the formula

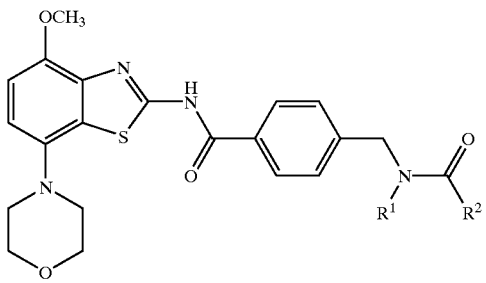

I wherein
$R^1$ is hydrogen or lower alkyl;
$R^2$ is lower alkyl, —$(CH_2)_n$—O-lower alkyl, —$C_{3-6}$-cycloalkyl or —$(CH_2)_n$—NR'R'';
R' and R'' are each independently hydrogen, lower alkyl or —$(CH_2)_n$—O-lower alkyl, or R' and R'' may form together with the N atom a pyrrolidine ring;
n is 1,2 or 3;
and to pharmaceutically acceptable acid addition salts thereof.

As used herein, the term "lower alkyl" denotes a saturated straight- or branched-chain alkyl group containing from 1 to 6 carbon atoms, for example, methyl, ethyl, propyl, isopropyl, n-butyl, i-butyl, 2-butyl, t-butyl and the like. Preferred lower alkyl groups are groups with 1–4 carbon atoms.

The term "halogen" denotes chlorine, iodine, fluorine and bromine.

The term "lower alkoxy" denotes a group wherein the alkyl residues is as defined above, and which is attached via an oxygen atom.

The term "pharmaceutically acceptable acid addition salts" embraces salts with inorganic and organic acids, such as hydrochloric acid, nitric acid, sulfuric acid, phosphoric acid, citric acid, formic acid, fumaric acid, maleic acid, acetic acid, succinic acid, tartaric acid, methane-sulfonic acid, p-toluenesulfonic acid and the like.

Preferred compounds of the present application are compounds of formula I, wherein $R^2$ is —$(CH_2)_n$—O-lower alkyl and $R^1$ is hydrogen or lower alkyl, for example the following compounds:

4-[(2-methoxy-acetylamino)-methyl]-N-(4-methoxy-7-morpholin-4-yl-benzothiazol-2-yl)-benzamide or
4-[(methoxyacetyl-methyl-amino)-methyl]-N-(4-methoxy-7-morpholin-4-yl-benzothiazol-2-yl)-benzamide.

Further preferred are compounds, wherein $R^2$ is $C_{3-6}$-cycloalkyl and $R^1$ is hydrogen or lower alkyl, for example the following compounds:

4-[(cyclopropanecarbonyl-amino)-methyl]-N-(4-methoxy-7-morpholin-4-yl-benzothiazol-2-yl)-benzamide,
4-[(cyclobutanecarbonyl-amino)-methyl]-N-(4-methoxy-7-morpholin-4-yl-benzothiazol-2-yl)-benzamide, 4-[(cyclopropanecarbonyl-methyl-amino)-methyl]-N-(4-methoxy-7-morpholin-4-yl-benzothiazol-2-yl)-benzamide or 4-[(cyclobutanecarbonyl-methyl-amino)-methyl]-N-(4-methoxy-7-morpholin-4-yl-benzothiazol-2-yl)-benzamide.

A further preferred group of compounds are those, wherein $R^2$ is lower alkyl and $R^1$ is hydrogen or lower alkyl, for example the following compounds:

N-(4-methoxy-7-morpholin-4-yl-benzothiazol-2-yl)-4-[(methyl-propionyl-amino)-methyl]-benzamide, N-(4-methoxy-7-morpholin-4-yl-benzothiazol-2-yl)-4-(propionylamino-methyl)-benzamide, 4-[(acetyl-methyl-amino)-methyl]-N-(4-methoxy-7-morpholin-4-yl-benzothiazol-2-yl)-benzamide, 4-(acetylamino-methyl)-N-(4-methoxy-7-morpholin-4-yl-benzothiazol-2-yl)-benzamide or 4-[(ethyl-propionyl-amino)-methyl]-N-(4-methoxy-7-morpholin-4-yl-benzothiazol-2-yl)-benzamide.

Further preferred compounds are those, wherein $R^2$ is the group —$(CH_2)_n$—NR'R" and $R^1$ is lower alkyl, 4-[(dimethylaminoacetyl-methyl-amino)-methyl]-N-(4-methoxy-7-morpholin-4-yl-benzothiazol-2-yl)-benzamide N-(4-methoxy-7-morpholin-4-yl-benzothiazol-2-yl)-4-{[methyl-(pyrrolidin-1-yl-acetyl)-amino]-methyl}-benzamide.

The present compounds of formula I and their pharmaceutically acceptable salts can be prepared by methods known in the art, for example, by processes described below, which process comprises a) reacting a compound of formula

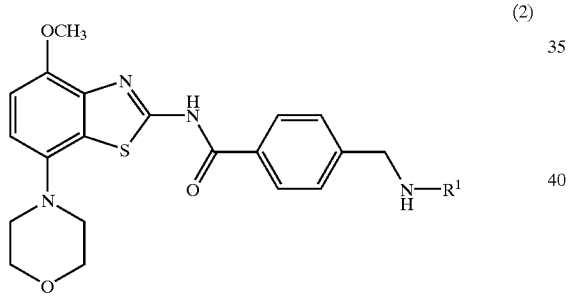

(2)

with a compound of formula

R²COCl  (3)

to a compound of formula

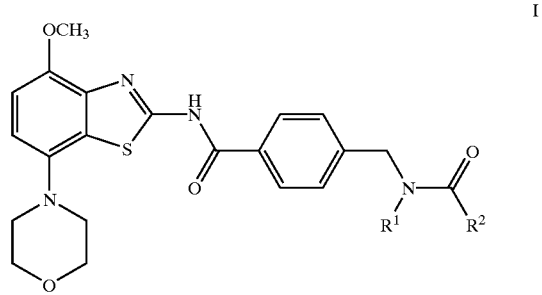

I wherein $R^1$ and $R^2$ are as defined above, and, if desired, converting the compounds obtained into pharmaceutically acceptable acid addition salts.

The compounds of formula I may be prepared in accordance with process variant a) and with the following scheme 1:

In scheme 1 the preparation of the starting material (4) and intermediates (5), (6), (7), (8) and (9) have been described in more detail in EP 00113219.0.

Scheme 1

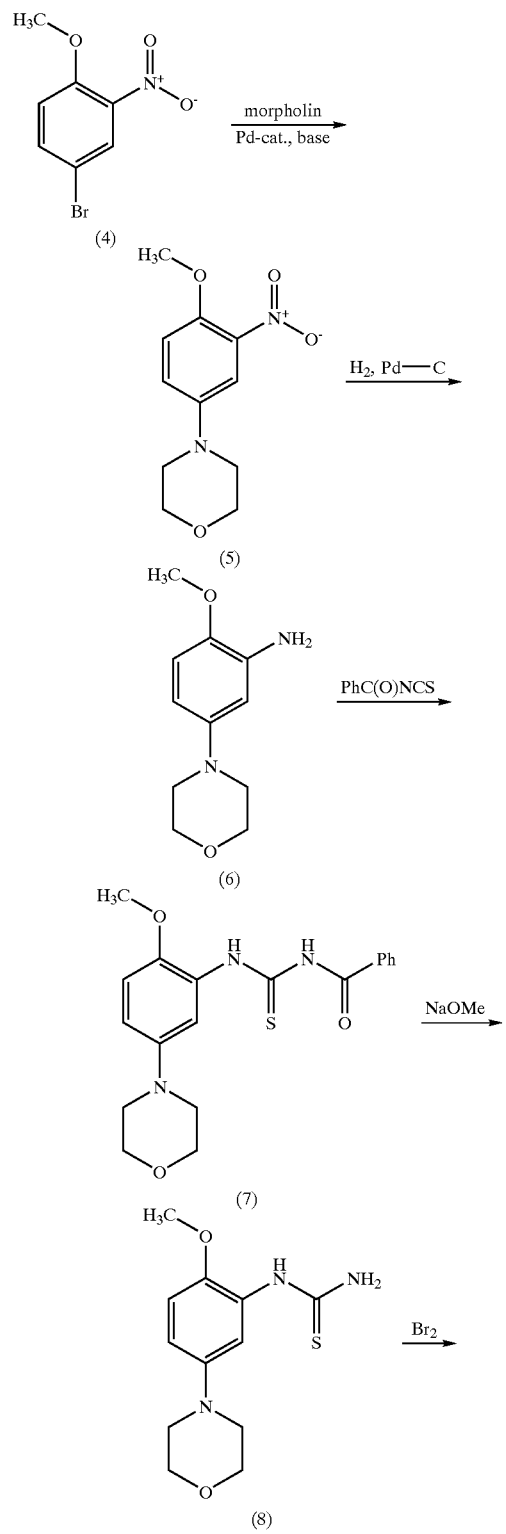

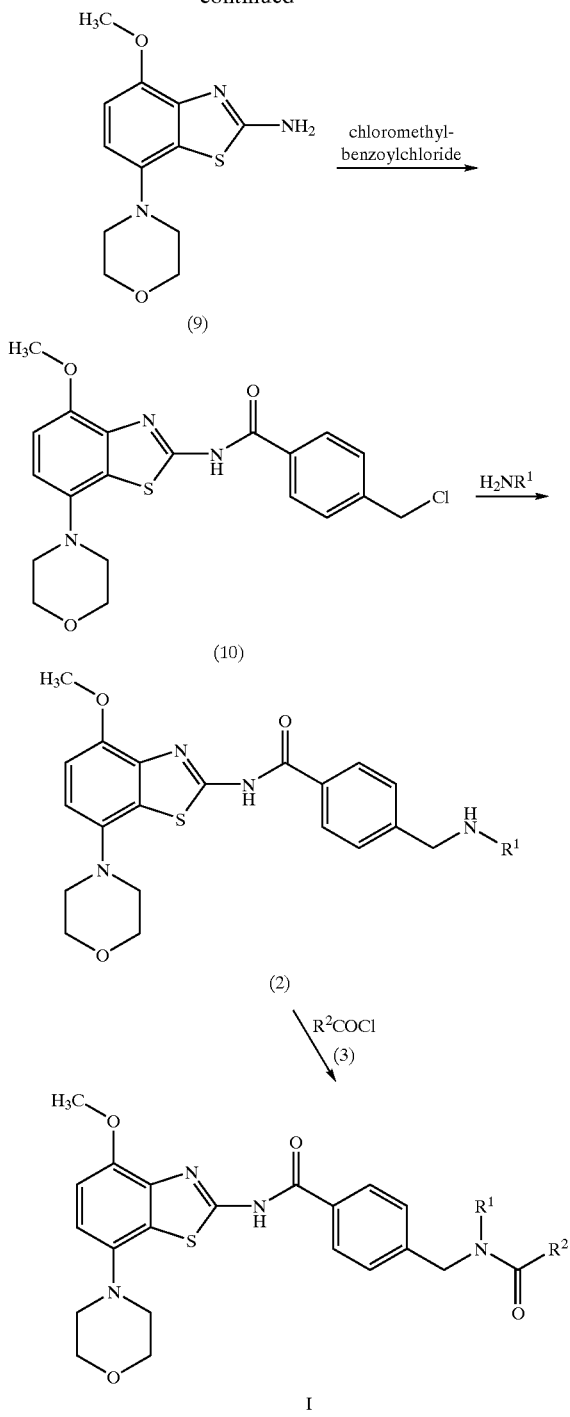

wherein $R^1$ and $R^2$ are defined above.

The compounds of formula I are prepared as follows:

A compound of formula (2), for example N-(4-methoxy-7-morpholin-4-yl-benzothiazol-2-yl)-4-aminomethyl-benzamide, dissolved in dichloromethane is treated with pyridine and with a compound of formula (3), for example methoxy-acetyl chloride or cyclopropanecarbonyl chloride, and stirred at ambient temperature for about 15 h. Saturated aqueous sodium carbonate is added, the phases are separated and the aqueous solution extracted. The combined organic phases are dried, filtered and evaporated to dryness and the corresponding compound of formula I is obtained.

Isolation and Purification of the Compounds

Isolation and purification of the compounds and intermediates described herein can be effected, if desired, by any suitable separation or purification procedure such as, for example, filtration, extraction, crystallization, column chromatography, thin-layer chromatography, thick-layer chromatography, preparative low or high-pressure liquid chromatography or a combination of these procedures. Specific illustrations of suitable separation and isolation procedures can be had by reference to the Preparations and Examples herein below. However, other equivalent separation or isolation procedures could, of course, also be used.

Salts of Compounds of Formula I

The compounds of formula I may be basic, for example in cases where the residue $R^2$ contains a basic group such as an aliphatic or aromatic amine moiety. In such cases the compounds of formula I may be converted to a corresponding acid addition salt.

The conversion is accomplished by treatment with at least a stoichiometric amount of an appropriate acid, such as hydrochloric acid, hydrobromic acid, sulfuric acid, nitric acid, phosphoric acid and the like, and organic acids such as acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluenesulfonic acid, salicylic acid and the like. Typically, the free base is dissolved in an inert organic solvent such as diethyl ether, ethyl acetate, chloroform, ethanol or methanol and the like, and the acid added in a similar solvent. The temperature is maintained between 0° C. and 50° C. The resulting salt precipitates spontaneously or may be brought out of solution with a less polar solvent.

The acid addition salts of the basic compounds of formula I may be converted to the corresponding free bases by treatment with at least a stoichiometric equivalent of a suitable base such as sodium or potassium hydroxide, potassium carbonate, sodium bicarbonate, ammonia, and the like.

The compounds of formula I and their pharmaceutically usable addition salts possess valuable pharmacological properties. Specifically, it has been found that the compounds of the present invention are adenosine receptor ligands and possess a high affinity towards the adenosine $A_{2A}$ receptor.

The compounds were investigated in accordance with the test given hereinafter.

Human Adenosine $A_{2A}$ Receptor

The human adenosine $A_{2A}$ receptor was recombinantly expressed in chinese hamster ovary (CHO) cells using the semliki forest virus expression system. Cells were harvested, washed twice by centrifugation, homogenised and again washed by centrifugation. The final washed membrane pellet was suspended in a Tris (50 mM) buffer containing 120 mM NaCl, 5 mM KCl, 2 mM $CaCl_2$ and 10 mM $MgCl_2$ (pH 7.4) (buffer A). The [$^3$H]-SCH-58261 (Dionisotti et al., 1997, Br J Pharmacol 121, 353; 1 nM) binding assay was carried out in 96-well plates in the presence of 2.5 µg of membrane protein, 0.5 mg of Ysi-poly-1-lysine SPA beads and 0.1 U adenosine deaminase in a final volume of 200 µl of buffer A. Non-specific binding was defined using xanthine amine congener (XAC; 2 µM). Compounds were tested at 10 concentrations from 10 µM –0.3 nM. All assays were conducted in duplicate and repeated at least two times.

Assay plates were incubated for 1 hour at room temperature before centrifugation and then bound ligand determined using a Packard Topcount scintillation counter. $IC_{50}$ values were calculated using a non-linear curve fitting program and Ki values calculated using the Cheng-Prussoff equation.

The preferred compounds show a pKi>8.8.

| Example No. | $hA_2$ (pKi) |
|---|---|
| 1 | 9.1 |
| 2 | 8.9 |
| 4 | 9.2 |
| 5 | 9.1 |
| 6 | 9.2 |
| 7 | 9.0 |
| 9 | 9.0 |
| 10 | 9.0 |
| 11 | 9.3 |
| 12 | 9.1 |
| 14 | 8.9 |
| 15 | 8.9 |
| 19 | 8.8 |

The compounds of formula I and the pharmaceutically acceptable salts of the compounds of formula I can be used as medicaments, e.g. in the form of pharmaceutical preparation. The pharmaceutical preparations can be administered orally, e.g. in the form of tablets, coated tablets, dragées hard and soft gelatine capsules, solutions, emulsions or suspensions. The administration can, however, also be effected rectally, e.g. in the form of suppositories, parenterally e.g. in the form of injection solutions.

The compounds of formula I can be processed with pharmaceutically inert, inorganic or organic carriers for the production of pharmaceutical preparations. Lactose, corn starch or derivatives thereof, talc, stearic acids or its salts and the like can be used, for example, as such carriers for tablets, coated tablets, dragées and hard gelatine capsules. Suitable carriers for soft gelatine capsule are, for example, vegetable oils, waxes, fats, semi-solid and liquid polyols and the like. Depending on the nature of the active substance no carriers are, however, usually required in the case of soft gelatine capsules. Suitable carriers for the production of solutions and syrups are, for example, water, polyols, glycerol, vegetable oil and the like. Suitable carriers for suppositories are, for example, natural or hardened oils, waxes, fats, semi-liquid polyols and the like.

The pharmaceutical preparations can, moreover, contain preservatives, solubilizers, stabilizers, wetting agents, emulsifiers, sweeteners, colorants, flavorants, salts for varying the osmotic pressure, buffers, masking agents or antioxidants. They can also contain still other therapeutically valuable substances.

Medicaments containing a compound of formula I or a pharmaceutically acceptable salt thereof and a therapeutically inert carrier are also an object of the present invention, as is a process for their production, which comprises bringing one or more compounds of formula I and/or pharmaceutically acceptable acid addition salts and, if desired, one or more other therapeutically valuable substances into a galenical administration form together with one or more therapeutically inert carriers.

In accordance with the invention compounds of formula I as well as their pharmaceutically acceptable salts are useful in the control or prevention of illnesses based on the adenosine receptor antagonistic activity, such as Alzheimer's disease, Parkinson's disease, neuroprotection, schizophrenia, anxiety, pain, respiration deficits, depression, asthma, allergic responses, hypoxia, ischaemia, seizure and substance abuse. Furthermore, compounds of the present invention may be useful as sedatives, muscle relaxants, antipsychotics, antiepileptics, anticonvulsants and cardiaprotective agents and for the production of corresponding medicaments.

The most preferred indications in accordance with the present invention are those, which include disorders of the central nervous system, for example the treatment or prevention of certain depressive disorders, neuroprotection and Parkinson's disease.

The dosage can vary within wide limits and will, of course, have to be adjusted to the individual requirements in each particular case. In the case of oral administration the dosage for adults can vary from about 0.01 mg to about 1000 mg per day of a compound of formula I or of the corresponding amount of a pharmaceutically acceptable salt thereof. The daily dosage may be administered as single dose or in divided doses and, in addition, the upper limit can also be exceeded when this is found to be indicated.

Tablet Formulation (Wet Granulation)

| | | mg/tablet | | | |
|---|---|---|---|---|---|
| Item | Ingredients | 5 mg | 25 mg | 100 mg | 500 mg |
| 1. | Compound of formula I | 5 | 25 | 100 | 500 |
| 2. | Lactose Anhydrous DTG | 125 | 105 | 30 | 150 |
| 3. | Sta-Rx 1500 | 6 | 6 | 6 | 30 |
| 4. | Microcrystalline Cellulose | 30 | 30 | 30 | 150 |
| 5. | Magnesium Stearate | 1 | 1 | 1 | 1 |
| | Total | 167 | 167 | 167 | 831 |

Manufacturing Procedure

1. Mix items 1, 2, 3 and 4 and granulate with purified water.
2. Dry the granules at 50° C.
3. Pass the granules through suitable milling equipment.
4. Add item 5 and mix for three minutes; compress on a suitable press.

Capsule Formulation

| | | mg/capsule | | | |
|---|---|---|---|---|---|
| Item | Ingredients | 5 mg | 25 mg | 100 mg | 500 mg |
| 1. | Compound of formula I | 5 | 25 | 100 | 500 |
| 2. | Hydrous Lactose | 159 | 123 | 148 | — |
| 3 | Corn Starch | 25 | 35 | 40 | 70 |
| 4. | Talc | 10 | 15 | 10 | 25 |
| 5. | Magnesium Stearate | 1 | 2 | 2 | 5 |
| | Total | 200 | 200 | 300 | 600 |

Manufacturing Procedure

1. Mix items 1, 2 and 3 in a suitable mixer for 30 minutes.
2. Add items 4 and 5 and mix for 3 minutes.
3. Fill into a suitable capsule.

EXAMPLE 1

4-[(2-Methoxy-acetylamino)-methyl]-N-(4-methoxy-7-morpholin-4-yl-benzothiazol-2-yl)-benzamide N-(4-Methoxy-7-morpholin-4-yl-benzothiazol-2-yl)-4-aminometyl-benzamide (100 mg, 0.24 mmol), dissolved in dichloromethane (5 ml) is treated with pyridine (29 µl, 0.36 mmol) and methoxy-acetyl chloride (24 µl, 0.32 mmol) and stirred at ambient temperature for 15 h. Saturated aqueous sodium carbonate (6 ml) is added, the phases are separated and the aqueous solution extracted twice with each 5 ml dichloromethane. The combined organic phases are dryed over sodium sulphate, filtered and evaporated to dryness. Flash chromatography (silica, eluent: dichloromethane containing 3% methanol) afforded the title compound as white crystals (71% yield). MS: m/e=471(M+H$^+$).

Following the general method of example 1 the compounds of examples 2 to 16 were prepared.

EXAMPLE 2

4-[(Methoxyacetyl-methyl-amino)-methyl]-N-(4-methoxy-7-morpholin-4-yl-benzothiazol-2-yl)-benzamide Using N-(4-methoxy-7-morpholin-4-yl-benzothiazol-2-yl)-4-methylaminomethyl-benzamide and methoxy-acetyl chloride, the title compound was prepared as yellow solid (83% yield). MS: m/e=485(M+H$^+$).

EXAMPLE 3

N-(4-Methoxy-7-morpholin-4-yl-benzothiazol-2-yl)-4-{[(3-methoxy-propionyl)-methyl-amino]-methyl}-benzamide Using N-(4-methoxy-7-morpholin-4-yl-benzothiazol-2-yl)-4-methylaminomethyl-benzamide and 3-methoxy-propionyl chloride, the title compound was prepared as light yellow crystals (46% yield). MS: m/e=499(M+H$^+$).

EXAMPLE 4

4-[(Cyclopropanecarbonyl-methyl-amino)-methyl]-N-(4-methoxy-7-morpholin-4-yl-benzothiazol-2-yl)-benzamide Using N-(4-methoxy-7-morpholin-4-yl-benzothiazol-2-yl)-4-methylaminomethyl-benzamide and cyclopropanecarbonyl chloride, the title compound was prepared as light yellow crystals (82% yield). MS: m/e=481(M+H$^+$).

EXAMPLE 5

4-[(Cyclobutanecarbonyl-methyl-amino)-methyl]-N-(4-methoxy-7-morpholin-4-yl-benzothiazol-2-yl)-benzamide Using N-(4-methoxy-7-morpholin-4-yl-benzothiazol-2-yl)-4-methylaminomethyl-benzamide and cyclobutanecarbonyl chloride, the title compound was prepared as light yellow crystals (59% yield). MS: m/e=495(M+H$^+$).

EXAMPLE 6

N-(4-Methoxy-7-morpholin-4-yl-benzothiazol-2-yl)-4-[(methyl-propionyl-amino)-methyl]-benzamide Using N-(4-methoxy-7-morpholin-4-yl-benzothiazol-2-yl)-4-methylaminomethyl-benzamide and propionyl chloride, the title compound was prepared as white crystals (59% yield). MS: m/e=469(M+H$^+$).

EXAMPLE 7

N-(4-Methoxy-7-morpholin-4-yl-benzothiazol-2-yl)-4-(propionylamino-methyl)-benzamide Using N-(4-methoxy-7-morpholin-4-yl-benzothiazol-2-yl)-4-aminomethyl-benzamide and propionyl chloride, the title compound was prepared as off-white crystals (34% yield). MS: m/e=455(M+H$^+$).

EXAMPLE 8

N-(4-Methoxy-7-morpholin-4-yl-benzothiazol-2-yl)-4-[(3-methoxy-propionylamino)-methyl]-benzamide Using N-(4-methoxy-7-morpholin-4-yl-benzothiazol-2-yl)-4-aminomethyl-benzamide and 3-methoxy-propionyl chloride, the title compound was prepared as white crystals (44% yield). MS: m/e=485(M+H$^+$).

EXAMPLE 9

4-[(Cyclopropanecarbonyl-amino)-methyl]-N-(4-methoxy-7-morpholin-4-yl-benzothiazol-2-yl)-benzamide Using N-(4-methoxy-7-morpholin-4-yl-benzothiazol-2-yl)-4-aminomethyl-benzamide and cyclopropanecarbonyl chloride, the title compound was prepared as light-yellow crystals (64% yield). MS: m/e=467(M+H$^+$).

EXAMPLE 10

4-[(Acetyl-methyl-amino)-methyl]-N-(4-methoxy-7-morpholin-4-yl-benzothiazol-2-yl)-benzamide Using N-(4-methoxy-7-morpholin-4-yl-benzothiazol-2-yl)-4-methylaminomethyl-benzamide and acetyl chloride, the title compound was prepared as white crystals (77% yield). MS: m/e=455(M+H$^+$).

EXAMPLE 11

4-[(Cyclobutanecarbonyl-amino)-methyl]-N-(4-methoxy-7-morpholin-4-yl-benzothiazol-2-yl)-benzamide Using N-(4-methoxy-7-morpholin-4-yl-benzothiazol-2-yl)-4-aminomethyl-benzamide and cyclobutanecarbonyl chloride, the title compound was prepared as off-white crystals (52% yield). MS: m/e=481(M+H$^+$).

EXAMPLE 12

4-(Acetylamino-methyl)-N-(4-methoxy-7-morpholin-4-yl-benzothiazol-2-yl)-benzamide Using N-(4-methoxy-7-morpholin-4-yl-benzothiazol-2-yl)-4-aminomethyl-benzamide and acetyl chloride, the title compound was prepared as white crystals (17% yield). MS: m/e=441(M+H$^+$).

EXAMPLE 13

4-[(Ethyl-methoxyacetyl-amino)-methyl]-N-(4-methoxy-7-morpholin-4-yl-benzothiazol-2-yl)-benzamide Using N-(4-methoxy-7-morpholin-4-yl-benzothiazol-2-yl)-4-ethylaminomethyl-benzamide and methoxy-acetyl chloride, the title compound was prepared as white solid (33% yield). MS: m/e=499(M+H$^+$).

EXAMPLE 14

4-[(Ethyl-propionyl-amino)-methyl]-N-(4-methoxy-7-morpholin-4-yl-benzothiazol-2-yl)-benzamide Using N-(4-methoxy-7-morpholin-4-yl-benzothiazol-2-yl)-4-ethylaminomethyl-benzamide and propionyl chloride, the title compound was prepared as white solid (47% yield). MS: m/e=483(M+H⁺).

EXAMPLE 15

4-[(Dimethylaminoacetyl-methyl-amino)-methyl]-N-(4-methoxy-7-morpholin-4-yl-benzothiazol-2-yl)-benzamide Using N-(4-methoxy-7-morpholin-4-yl-benzothiazol-2-yl)-4-methylaminomethyl-benzamide and dimethylaminoacetyl chloride, the title compound was prepared as light yellow crystals (46% yield). MS: m/e=498(M+H⁺).

EXAMPLE 16 (INTERMEDIATE)

4-[(Chloroacetyl-methyl-amino)-methyl]-N-(4-methoxy-7-morpholin-4-yl-benzothiazol-2-yl)-benzamide Using N-(4-methoxy-7-morpholin-4-yl-benzothiazol-2-yl)-4-methylaminomethyl-benzamide and chloroacetyl chloride, the title compound was prepared as yellow foam (51% yield). MS: m/e=489 (M+H⁺).

EXAMPLE 17

N-(4-Methoxy-7-morpholin-4-yl-benzothiazol-2-yl)-4-(2-oxo-pyrrolidin-1-yl-methyl)-benzamide Sodium hydride (48 ms, 0.48 mmol, 60% in mineral oil) are suspended in dimethyl formamide (2.0 ml) and at 0° C. treated with pyrrolidin-2-one. After stirring for 1 h at 50° C., N-(4-methoxy-7-morpholin-4-yl-benzothiazol-2-yl)-4-chloromethyl-benzamide (200 mg, 0.48 mmol) was added and the solution stirred for 5 h at 80° C. Removal of the volatile components in vacuo and flash chromatography (silica, eluent dichloromethane/methanol 19:1) afforded the title compound as off-white crystals (86% yield). MS: m/e= 467(M+H+).

EXAMPLE 18

4-[({[(2-Methoxy-ethyl)-methyl-amino]-acetyl}-methyl-amino)-methyl]-N-(4-methoxy-7-morpholin-4-yl-benzothiazol-2-yl)-benzamide 4-[(Chloroacetyl-methyl-amino)-methyl]-N-(4-methoxy-7-morpholin-4-yl-benzothiazol-2-yl)-benzamide (100 mg, 205 mmol) are dissolved in N-(2-methoxyethyl)-methylamine (1.8 ml, 21 mmol) and the mixture stirred for 2 h at 55° C. Saturated aqueous sodium hydrogen carbonate is added (50 ml) and dichloromethane (50 ml) are added, the phases are separated and the aqueous phase extracted twice with 50 ml dichloromethane. The combined organic layers are dried with magnesium sulfate and evaporated. Flash chromatography (silica, dichloromethane containing 5% methanol) afforded the title compound as white crystals (74% yield), mp 171–173° C. MS: m/e=542 (M+H+).

Following the general method of example 18 the compound of example 19 was prepared.

EXAMPLE 19

N-(4-Methoxy-7-morpholin-4-yl-benzothiazol-2-yl)-4-{[methyl-(pyrrolidin-1-yl-acetyl)-amino]-methyl}-benzamide Using 4-[(Chloroacetyl-methyl-amino)-methyl]-N-(4-methoxy-7-morpholin-4-yl-benzothiazol-2-yl)-benzamide and pyrrolidine the title compound was obtained as white crystals (61% yield), mp 114–116° C.). MS: m/e=524 (M+H+).

We claim:
1. A compound of the formula I

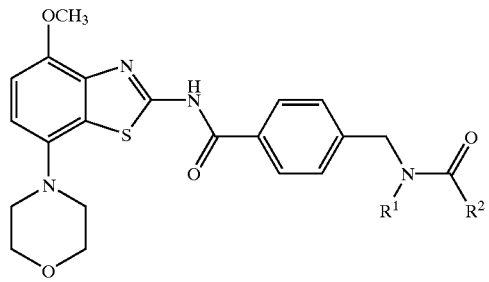

wherein
R¹ is hydrogen or lower alkyl;
R² is lower alkyl, —(CH₂)ₙ—O-lower alkyl, —C₃₋₆-cycloalkyl or —(CH₂)ₙ—NR'R";
R' and R" are each independently hydrogen, lower alkyl or —(CH₂)ₙ—O-lower alkyl, or R' and R" may form together with the N atom a pyrrolidine ring;
n is 1, 2 or 3;
and pharmaceutically acceptable acid addition salts thereof.
2. The compound according to claim 1, wherein R² is —(CH₂)ₙ—O-lower alkyl and R¹ is hydrogen or lower alkyl.
3. The compound according to claim 2, wherein the compound is selected from the group consisting of
  4-[(2-methoxy-acetylamino)-methyl]-N-(4-methoxy-7-morpholin-4-yl-benzothiazol-2-yl)-benzamide and
  4-[(methoxyacetyl-methyl-amino)-methyl]-N-(4-methoxy-7-morpholin-4-yl-benzothiazol-2-yl)-benzamide.
4. The compound according to claim 1, wherein R² is C₃₋₆-cycloalkyl and R¹ is hydrogen or lower alkyl.
5. The compound according to claim 4, wherein the compound is selected from the group consisting of
  4-[(cyclopropanecarbonyl-amino)-methyl]-N-(4-methoxy-7-morpholin-4-yl-benzothiazol-2-yl)-benzamide,
  4-[(cyclobutanecarbonyl-amino)-methyl]-N-(4-methoxy-7-morpholin-4-yl-benzothiazol-2-yl)-benzamide,
  4-[(cyclopropanecarbonyl-methyl-amino)-methyl]-N-(4-methoxy-7-morpholin-4-yl-benzothiazol-2-yl)-benzamide and
  4-[(cyclobutanecarbonyl-methyl-amino)-methyl]-N-(4-methoxy-7-morpholin-4-yl-benzothiazol-2-yl)-benzamide.
6. The compound according to claim 1, wherein R² is lower alkyl and R¹ is hydrogen or lower alkyl.
7. The compound according to claim 6, wherein the compound is selected from the group consisting of
  N-(4-methoxy-7-morpholin-4-yl-benzothiazol-2-yl)-4-[(methyl-propionyl-amino)-methyl]-benzamide,
  N-(4-methoxy-7-morpholin-4-yl-benzothiazol-2-yl)-4-(propionylamino-methyl)-benzamide,
  4-[(acetyl-methyl-amino)-methyl]-N-(4-methoxy-7-morpholin-4-yl-benzothiazol-2-yl)-benzamide,
  4-(acetylamino-methyl)-N-(4-methoxy-7-morpholin-4-yl-benzothiazol-2-yl)-benzamide and 4-[(ethyl-propionyl-amino)-methyl]-N-(4-methoxy-7-morpholin-4-yl-benzothiazol-2-yl)-benzamide.

8. The compound according to claim 1, wherein $R^2$ is the group —(CH$_2$)$_n$—NR'R" and $R^1$ is lower alkyl.

9. The compound according to claim 8, wherein the compound is selected from the group consisting of 4-[(dimethylaminoacetyl-methyl-amino)-methyl]-N-(4-methoxy-7-morpholin-4-yl-benzothiazol-2-yl)-benzamide and N-(4-methoxy-7-morpholin-4-yl-benzothiazol-2-yl)-4-{[methyl-(pyrrolidin-1-yl-acetyl)-amino]-methyl}-benzamide.

10. A process for preparing a compound of formula I as defined in claim 1, which process comprises reacting a compound of formula

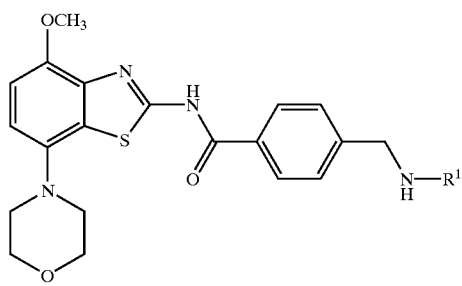

(2)

with a compound of formula

R$^2$COCl   (3)

to yield a compound of formula

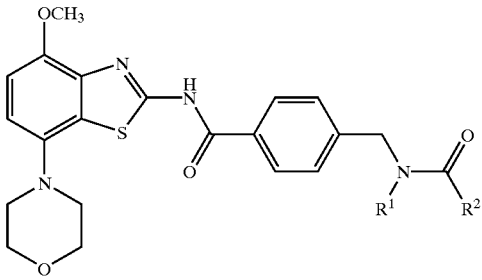

I wherein R$^1$ and R$^2$ are as defined in claim 1.

11. The process according to claim 10, further comprising converting the compounds obtained into pharmaceutically acceptable acid addition salts by treatment with an appropriate acid.

12. A method of treating a disease mediated by the adenosine receptor comprising administering to a patient in need of such treatment, an effective amount of a compound of the formula I

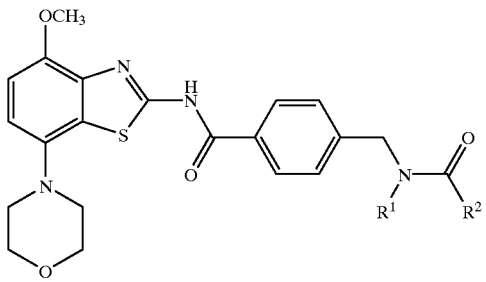

I wherein
R$^1$ is hydrogen or lower alkyl;
R$^2$ is lower alkyl, —(CH$_2$)$_n$—O-lower alkyl, —C$_{3-6}$-cycloalkyl or —(CH$_2$)$_n$—NR'R";
R' and R" are each independently hydrogen, lower alkyl or —(CH$_2$)$_n$—O-lower alkyl, or R' and R" may form together with the N atom a pyrrolidine ring;
n is 1, 2 or 3;
and pharmaceutically acceptable acid addition salts thereof.

13. The method according to claim 12, wherein said disease is selected from at least one of Alzheimer's disease, Parkinson's disease, Huntington's disease, neuroprotection, schizophrenia, anxiety, pain, respiration deficits, depression, drug addiction, asthma, allergic responses, hypoxia, ischaemia, seizure, and attention deficit hyperactivity disorder.

14. The method according to claim 12, wherein said adenosine receptor is the A$_{2A}$ receptor.

15. The method according to claim 14, wherein said disease is selected from the group consisting of Alzheimer's disease, depression, drug addiction, neuroprotection, Parkinson's disease, and attention deficit hyperactivity disorder.

16. A pharmaceutical composition comprising a pharmaceutically effective amount of a compound of the formula I

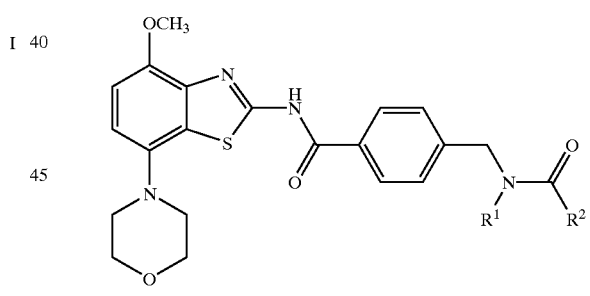

I wherein
R$^1$ is hydrogen or lower alkyl;
R$^2$ is lower alkyl, —(CH$_2$)$_n$—O-lower alkyl, —C$_{3-6}$-cycloalkyl or —(CH$_2$)$_n$—NR'R";
R' and R" are each independently hydrogen, lower alkyl or —(CH$_2$)$_n$—O-lower alkyl, or R' and R" may form together with the N atom a pyrrolidine ring;
n is 1, 2 or 3;
and pharmaceutically acceptable acid addition salts thereof; and a pharmaceutically acceptable carrier.

* * * * *

UNITED STATES PATENT AND TRADEMARK OFFICE
CERTIFICATE OF CORRECTION

PATENT NO. : 6,624,163 B2
DATED : September 23, 2003
INVENTOR(S) : Alexander Flohr et al.

It is certified that error appears in the above-identified patent and that said Letters Patent is hereby corrected as shown below:

<u>Title page</u>,
Item [73], Assignee, delete "Hoffman-La Roche Inc., Nutley, NJ (US)" and insert
-- Hoffmann-La Roche Inc., Nutley, NJ (US) --.

<u>Column 16</u>,
Line 18, delete "R' and R" areeach independently hydrogen, lower alkyl or" and insert
-- R' and R" are each independently hydrogen, lower alkyl or --.

Signed and Sealed this

Seventeenth Day of February, 2004

JON W. DUDAS
*Acting Director of the United States Patent and Trademark Office*